(12) United States Patent
Furniss

(10) Patent No.: US 7,975,853 B2
(45) Date of Patent: Jul. 12, 2011

(54) METHOD AND APPARATUS FOR SORTING SMALL FOOD ITEMS FOR SOFTNESS

(76) Inventor: Gregory William Furniss, Ohaupo (NZ)

( * ) Notice: Subject to any disclaimer, the term of this patent is extended or adjusted under 35 U.S.C. 154(b) by 1408 days.

(21) Appl. No.: 11/428,529

(22) Filed: Jul. 3, 2006

(65) Prior Publication Data

US 2008/0003333 A1    Jan. 3, 2008

(51) Int. Cl.
*B07C 5/00* (2006.01)
(52) U.S. Cl. .......................... 209/599; 209/640
(58) Field of Classification Search .............. 209/552, 209/559, 599, 640; 73/79; 426/231
See application file for complete search history.

(56) References Cited

U.S. PATENT DOCUMENTS

| 3,127,016 | A | * | 3/1964 | Baigent | 209/590 |
| 3,559,805 | A | * | 2/1971 | Cragg et al. | 209/600 |
| 3,788,466 | A | * | 1/1974 | Wilson et al. | 209/599 |
| 4,625,872 | A | * | 12/1986 | DeLacy et al. | 209/557 |
| 4,666,046 | A | * | 5/1987 | Manzer | 209/599 |

FOREIGN PATENT DOCUMENTS

DE     3900450 A1 *  7/1990
* cited by examiner

*Primary Examiner* — Joseph C Rodriguez
(74) *Attorney, Agent, or Firm* — Young & Thompson

(57) ABSTRACT

The invention relates to the high speed non-destructive sorting of small food items for softness. The food item is conveyed on a series of belts designed to accurately drop the food item onto a flexible surface at an oblique angle. Accelerometers mounted under the flexible surface generate impact waveforms, which are computer analysed to both detect the item landing position and enable comparison with an operator-selected softness threshold level. Within a few milliseconds of the food item contacting the flexible surface it continues to drop past a rejection point. If determined by analysis to be soft, it is ejected to a waste conveyor.

17 Claims, 2 Drawing Sheets

METHOD AND APPARATUS FOR SORTING SMALL FOOD ITEMS FOR SOFTNESS

BACKGROUND OF THE INVENTION

The invention relates to the process of non-destructively sorting small items by assessment of the condition of softness, particularly for small fruits or vegetables. Small food items are often sorted prior to sale or consumption on the basis of their softness. Products such as blueberries, olives, cranberries, cherries, grape tomatoes, cherry tomatoes require such sorting. There are several mechanical systems used with varying degrees of success. These systems generally use the principle of soft fruit not rolling as freely as firm fruit. This is fairly effective when removing very soft material however it is not very sensitive for a food item that is only slightly soft. This product is often sorted by hand which is labour intensive and can lead to further damage. Very firm fruit such as cranberries are mechanically sorted with a berry bounce system, which is effective however it is often too slow for large-scale packers. Most small fruit grading and packing lines are capable of packing over 5000 lb per hour, which is well beyond the capacity of the cranberry bounce softness sorter.

The main reason for wanting to sort out the soft food items is to increase the product shelf life. The soft product tends to have a higher incidence of rots and decay. Softness can also be a function of maturity and over maturity can also contribute to reduce shelf life. Such food items are also commonly subject to pricing regimes that are product-quality dependent, so to match product quality to market expectations usually results in maximising returns to the product owner.

To address the quality matching issue, a product sorter is described. Any symmetrical item within a size range similar to a berry can be sorted on the basis of its softness using this method and apparatus. Other items may also be suitable, provided the fall involved in its characterisation is insufficient to create tissue damage causing subsequent susceptibility to premature quality degradation. The preferred embodiment of the invention utilises a shallow angle rebound (ricochet) so as to minimise the deformation energy imparted to the item during rebound, thereby minimising risk of tissue damage, while yet being sufficient to extract its ricochet energy signature.

This invention is superficially similar in principle to U.S. Pat. No. 6,541,725 (Acoustical apparatus and method for sorting objects) in which the procedure of rebounding an item off a surface is optimised for hard items such as nuts, which emit an acoustic deformation energy signature after leaving the impact surface. That technique requires a rigid and immovable rebound surface, and the introduction of a time delay after the impact to ensure the deformation energy signature is sampled at the appropriate time after rebound. Additionally, the deformation energy is released by acoustic radiation in air, therefore appropriately detected by microphone. In contrast, this invention extracts the deformation energy signature by conducted energy transfer while the food item impacts a resiliently mounted rebound surface and remains in contact with that surface. In this aspect its detection method is similar to a cherry sorter impact sensor (Younce & Davis, 1995, ASAE) but necessarily and fully integrates trajectory control into its functioning.

DETAILED DESCRIPTION OF THE INVENTION

Figure 1:
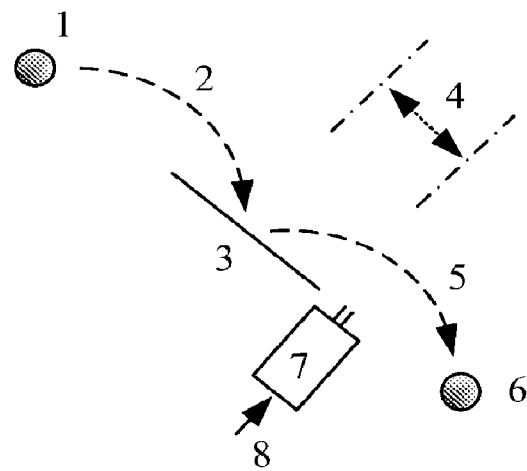
FIG. 1 schematically shows an elevation of an exemplary embodiment of the invention, illustrating the trajectory of an item of softness less than the threshold value.

The invention comprises both a method and apparatus for sorting small food items for softness, which: accurately projects 2 a food item 1 onto a target plate 3, obtains a measurement of food item softness from instrumentation 21 associated with the target plate 3, generates an accept/reject decision 26 based on the comparison 25 between the measured softness and a pre-selected decision threshold 32, to either during ricochet trajectory 5 allow the item 1 to remain in the flow of accepted items 6, or if required, during ricochet trajectory 9, actuate 27 a rejection procedure 10 to divert 11 the item 12 to waste.

The apparatus comprises a target trajectory control system, in which the horizontal plane alignment for target accuracy is determined by a system of moveable belts 13; the belts function as a sequencing conveyor to deliver items 1 to a target 3 one at a time; the vertical plane target trajectory 2 control is achieved by a combination of mechanical and electronic and computational means; the vertical plane target trajectory 2 control is achieved by varying the moveable belt 13 velocity by a variable speed drive system 31; the vertical plane target trajectory 2 control system achieves consistent targeting accuracy by varying the inverted V belt velocity under control by averaged data feedback 28 derived from the impact analysis system 21 and software 22, whereby if the impact location tends towards the target plate near-edge 15 the belt velocity is increased, and if the impact location tends towards the far plate edge 17 the belt velocity is reduced, and if the impact location is on target centre 16 the belt velocity is not changed.

Figure 2:
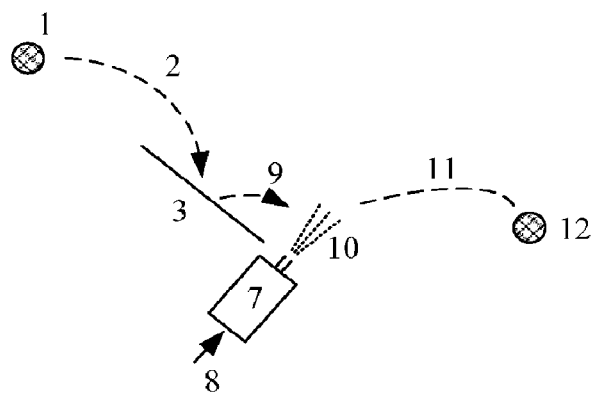
FIG. 2 shows the trajectory of an item of softness greater than the threshold value, and its diversionary means.
Figure 3:
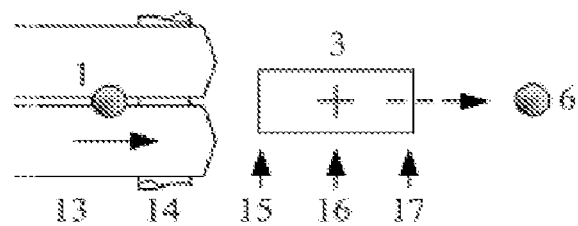
FIG. 3 shows the exemplary embodiment in plan view, and illustrating the conveyor belt profile.
Figure 4:
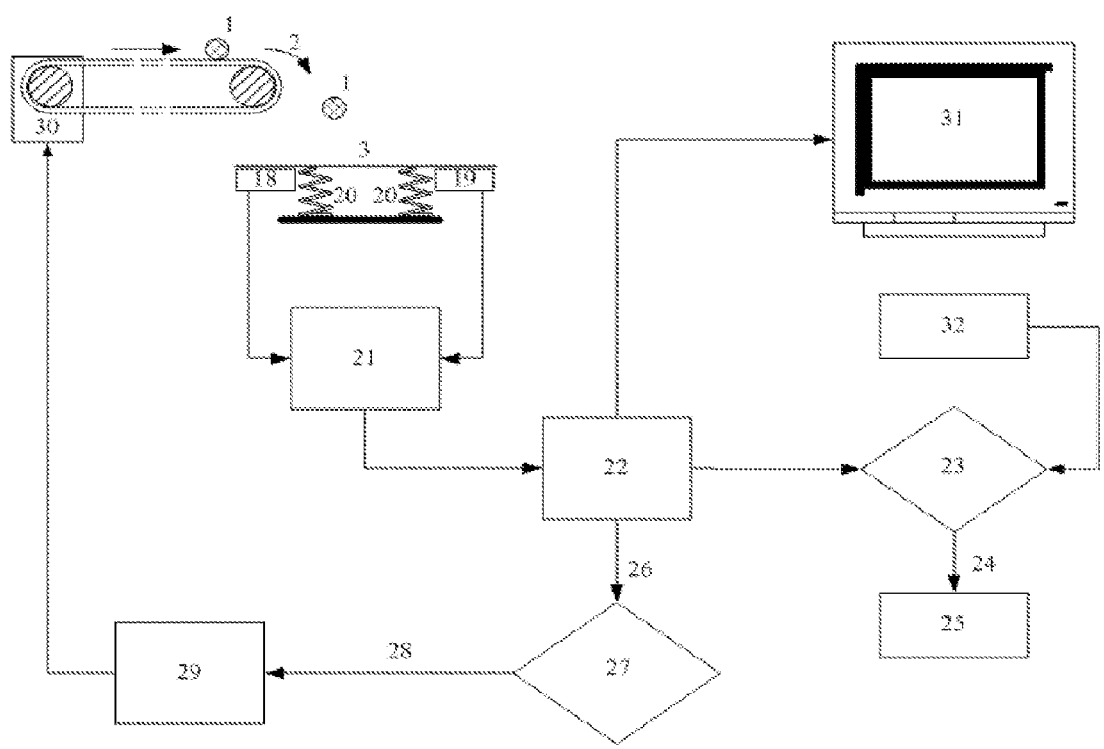
FIG. 4 shows the apparatus in block diagram form.

An impact analysis system, comprising an instrumented target plate 3, and associated electronic signal processing and control system hardware 21 and software 22, in which the instrumented target plate 3 comprises a resiliently 20 mounted rigid plate 3 containing multiple accelerometers 18,19; each accelerometer generates electrical signals representing the food item impact; purpose-designed but otherwise conventional electronics amplify and convert the signals to digital form; purpose-designed but otherwise conventional software operating on a conventional digital signal processor system extracts real-time data from those digitised signals; the real-time data from each accelerometer pair on an impact plate 3 is compared 29; the real-time data is analysed for magnitude of initial reverse-phase signal generated by off-centre impact; analysis of the signals generated during target impact is transformed into numbers representing item softness; the softness data is compared 25 with the selected softness threshold and thereby transformed into a decision to accept (see FIG. 1) or reject 26 (see FIGS. 2 & 4) the food item; from the reverse-phase data is generated an "item off-centre" data value which, averaged over a short time period, is transformed into a feedback signal 30 to influence said sequencing conveyor velocity to maintain target accuracy; that feedback signal is converted into a variable delay 4 influencing air jet timing.

A soft item rejection system, in which a soft item 12 is ejected during ricochet 9 from the said target plate 3 by pneumatic means 7, 8, 10; the pneumatic means is a conventional electrically controlled pneumatic actuator 7 supplied with high pressure air 8; the pneumatic actuator 7 releases a high velocity air jet 10 if the item is identified as above the selected softness threshold; the air jet 10 accelerates 11 the item 12 towards a reject conveyor of conventional design.

A system of output conveyors of conventional design to collect selected items, item debris, and rejected items.

An operator interface 27 of conventional design, in which numeric softness data may be displayed; the softness selection threshold may be adjusted; other operator commands may be input; and all other analytic results may be accessed.

The described embodiments of the invention are intended to be merely exemplary and numerous variations and modifications will be apparent to those skilled in the art. All such variations and modifications are intended to be within the scope of the present invention as defined in this description.

What is claimed is:

1. A method to measure and selectively divert near-spherical items from a single stream into two streams on the basis of softness of the items, the method comprising the steps of:
    using a controlled trajectory to project each of the items, from a single stream of items, onto a center of a ricochet energy signature analytic surface;
    evaluating a softness condition of each near-spherical item by determining a measurement of the softness of each near-spherical item by analysis of a corresponding ricochet energy signature of each item,
    said ricochet energy signature arising from a glancing impact of each item travelling via the controlled trajectory against the ricochet energy signature analytic surface,
    said ricochet energy signature analytic surface being inclined, and
    said ricochet energy signature analytic surface being resiliently mounted;
    selectively pneumatically diverting the near-spherical items into one stream of two streams on the basis of the determined softness of the items; and
    maintaining targeting accuracy of the items by selectively adjusting the controlled trajectory of the near-spherical items onto the center the ricochet energy signature analytic surface on the basis of the determined measurement of the softness of the items.

2. The method as claimed in claim 1, wherein the said ricochet energy signature analytic surface constitutes an instrumented target.

3. The method as claimed in claim 2, wherein the said instrumented target contains force measuring devices.

4. The method as claimed in claim 3, wherein the said force measurement devices are accelerometers.

5. The method as claimed in claim 4 wherein the said force measurement devices convert a mechanical ricochet energy signature into an electrical analogue.

6. The method as claimed in claim 5, wherein the said mechanical ricochet energy signature is analysed and assigned a softness value to an item which is then compared to a pre-selected threshold value and thereby transformed into a computed decision to accept or reject said item.

7. The method as claimed in claim 6, wherein,
    the said items are food items, and
    the diverting is pneumatic so that selected ones of the items, travelling to a first of the two steams, are pneumatically diverted into a second of the two streams.

8. An apparatus to measure and selectively divert near-spherical items from a single stream into two streams on the basis of softness of the items, said apparatus comprising:
    flexible belts configured for carrying the items in a single stream, said flexible belts being configured for operation at varying velocities to project the items from the belts;
    a ricochet energy signature analytic surface configured for effecting measurement of a softness of each item by analysis of a corresponding ricochet energy signature of each item,
    the belts operatively arranged to project each of the items in a controlled trajectory from a single stream of items, onto the center of a ricochet energy signature analytic surface, wherein targeting accuracy of the items is maintained by selectively adjusting the controlled trajectory of the near-spherical items onto the center the ricochet energy signature analytic surface on the basis of the determined measurement of the softness of the items,
    said ricochet energy signature analytic surface being inclined,
    said ricochet energy signature analytic surface being resiliently mounted, and
    said ricochet energy signature analytic surface including force measurement devices,
    wherein said ricochet energy signature arises from a glancing impact of each item travelling via a controlled trajectory against said ricochet energy signature analytic surface, said ricochet energy signature analytic surface evaluating a softness condition of each near-spherical item by determining the measurement of the softness of each near-spherical item by analysis of the corresponding ricochet energy signature of each item; and
    a pneumatic device configured to selectively pneumatically divert the near-spherical items into one stream of two streams on the basis of the determined softness of the items.

9. The apparatus as claimed in claim 8, wherein the said ricochet energy signature analytic surface constitutes an instrumented target.

10. The apparatus as claimed in claim 9, wherein the said instrumented target is configured to receive an item projected at the said instrumented target by the flexible belts.

11. The apparatus as claimed in claim 10, wherein the flexible belts are configured to have varying belt velocity proportional to item deviation from a target center to enable items to be accurately projected at the instrumented target.

12. The apparatus as claimed in claim 10, wherein,
    said flexible belts define a variable speed food sequencing conveyor.

13. The apparatus as claimed in claim 10,
    wherein said pneumatic device comprises a pneumatic actuator located downstream of said ricochet energy signature analytic surface,
    wherein the pneumatic actuator is controlled by said ricochet energy signature from said ricochet energy signature analytic surface, to divert selected ones of the items, from travelling onward to a first of the two steams, into a second of the two streams.

14. The apparatus as claimed in claim 8, wherein the said force measurement devices convert a mechanical ricochet energy signature into an electrical analogue.

15. The apparatus as claimed in claim 14, wherein the said mechanical ricochet energy signature is analysed and assigned a softness value which is then compared to a preselected threshold value and thereby transformed into a computed decision to accept or reject that item.

16. The apparatus as claimed in claim 15, in which the items are foods, and the said mechanical ricochet energy signature is analysed via the items hitting the ricochet energy signature analytic surface where the said force measurement devices comprise accelerometers.

17. The apparatus as claimed in claim 8, wherein,
the items are food, and
a measurement of the softness of each food item, from the ricochet energy signature analytic surface, is used to control the velocity of the flexible belts to maintain targeting accuracy of the items from the flexible belts onto a target center of the ricochet energy signature analytic surface.

\* \* \* \* \*